United States Patent [19]

Ries et al.

[11] 4,164,150

[45] * Aug. 14, 1979

[54] SYSTEM FOR INSPECTING TUBES OR PIPES BY MEANS FOR ULTRASONICS

[75] Inventors: Karl Ries, Mülheim; Kurt Hannoschöck, Sonsbeck; Gunter Simoneit, Mülheim, all of Fed. Rep. of Germany

[73] Assignee: Mannesmann Aktiengesellschaft, Dusseldorf, Fed. Rep. of Germany

[*] Notice: The portion of the term of this patent subsequent to Nov. 15, 1994, has been disclaimed.

[21] Appl. No.: 803,362

[22] Filed: Jun. 3, 1977

[30] Foreign Application Priority Data

Jun. 3, 1976 [DE] Fed. Rep. of Germany ....... 2625311

[51] Int. Cl.$^2$ ............................................. G01N 29/04
[52] U.S. Cl. .................................................. 73/644
[58] Field of Search ................. 73/622, 625, 626, 628, 73/640, 641, 644

[56] References Cited

U.S. PATENT DOCUMENTS

| | | | |
|---|---|---|---|
| 3,074,268 | 1/1963 | Rafferty et al. | 73/644 |
| 3,375,706 | 4/1968 | Pandelis et al. | 73/622 X |
| 3,828,609 | 8/1974 | Furon et al. | 73/625 X |
| 3,913,386 | 10/1975 | Saglio | 73/644 |
| 4,058,000 | 11/1977 | Ries et al. | 73/644 |

FOREIGN PATENT DOCUMENTS 175300 2/1966 U.S.S.R. ............................... 73/71.54 S

*Primary Examiner*—Herbert Goldstein
*Attorney, Agent, or Firm*—Smyth, Pavitt, Siegemund, Jones & Martella

[57] ABSTRACT

A plurality of water tanks hold a plurality of ultrasonic transducers, each providing a different angle of incidence for ultrasonic radiation for a tube or pipe passing through the tank. Water of a specific temperature is fed to the particular tank being used and in conjunction with a particularly oriented transducer, a particular test angle of refraction is established. Through a particular range of different transducer orientations in conjunction with a temperature range from about 5° to 40° C., a rather wide range of possible refraction angles can be established.

5 Claims, 3 Drawing Figures

SYSTEM FOR INSPECTING TUBES OR PIPES BY MEANS FOR ULTRASONICS

BACKGROUND OF THE INVENTION

The present invention refers to equipment for ultrasonic testing of tubes or pipes and more particularly, the invention relates to a test stand for the ultrasonic testing and inspection of tubes or pipes in which pipes and tubes of different wall thickness-to-diameter values (T/D ratios) can be tested.

The testing of tubes or pipes as to flaws and defects, using ultrasonic beams and using further the immersion technique, i.e. using water as a coupler fluid for coupling the ultrasonic transducer to the pipes material, require a specific angle of incidence of the ultrasonic beam in relation to a normal on the tube or pipe surface, through the point of entrance of the beam into the wall of the tubes. Upon entering the tube's wall, the test beam undergoes refraction because the tube/fluid interface is also a discontinuity as far as the propagation of sonic and ultrasonic vibrations is concerned. The angle of refracted radiation beam to that normal will in the following be called the test angle of refraction, because it results from refraction of the incident test beam as it is being refracted via in the water-tube material interface. It was found that for each particular type of tube and pipe, as defined by a specific T/D ratio, and for a specific material (e.g. steel), there is but one such test angle of refraction for a useful test beam. However, depending upon the T/D ratio, the test angle of refraction varies greatly and may be as low as 33°, as high as almost 90° C., this being true particularly if transversal waves are being employed.

In our co-pending application, Ser. No. 770,587, filed Feb. 22, 1977, now U.S. Pat. No. 4,058,000, we have proposed a method to vary the test angle of refraction through temperature control of the coupler fluid. The disclosure of that application is incorporated by reference in this application.

DESCRIPTION OF THE INVENTION

It is an object of the present invention to provide a new and improved system which permits rapid selection of the needed test angle of refraction covering a very wide range or responding to a wide range of different pipes and here particularly a wide range of T/D ratios.

It is another object of the present invention to make more fully use of the method as disclosed in the above-identified co-pending application, for the purposes of wide range adjustment in an ultrasonic test stand for tubes and pipes.

In accordance with the preferred embodiment of the present invention, it is suggested to provide a plurality of test head tanks, each containing one or more ultrasonic test transducers and each being mounted in the respective tank at a fixed orientation. These orientations differ for the various transducers in the same as well as in different test tanks. In addition, sources for cold and hot water are provided as well as means for mixing appropriate amounts of hot and cold water for charging one of thest test tanks, being used for test purposes. The angle of incidence of the test beam as provided by a particular transdcuer is fixed, but the angle of refraction varies in accordance with the selected tank water temperature. Each transducer as fixedly mounted, in conjunction with a rather wide range of temperatures for the tank water, permits establishing different test angles of refraction within a particular range. The different transducer orientations in conjunction with the same temperature range establish different ranges for the test angle of refraction to be used in inspecting a wide variety of pipes. The transducer themselves have orientations defined by descrete and fixed angles; the temperature adjustment of the tank water permits stepless coverage of the entire range of angles needed.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows the following equipment. A roller track 4 is provided for moving tubes or pipes to be tested in longitudinal direction into and through the test station 5. The system further includes a roller track 5 for withdrawing such a tube or pipe from the test stands. In the essence, the test stand is comprised of a frame which includes two rails 3. A plurality of altogether three carriages 1, 1a, and 1b, are mounted for movement on the rails 3. The rails are oriented to provide for carriage movement transversely to the direction of movement of a pipe through the station which is also the direction of movement imparted upon objects by the roller tracks 4 and 5.

Figure 3:
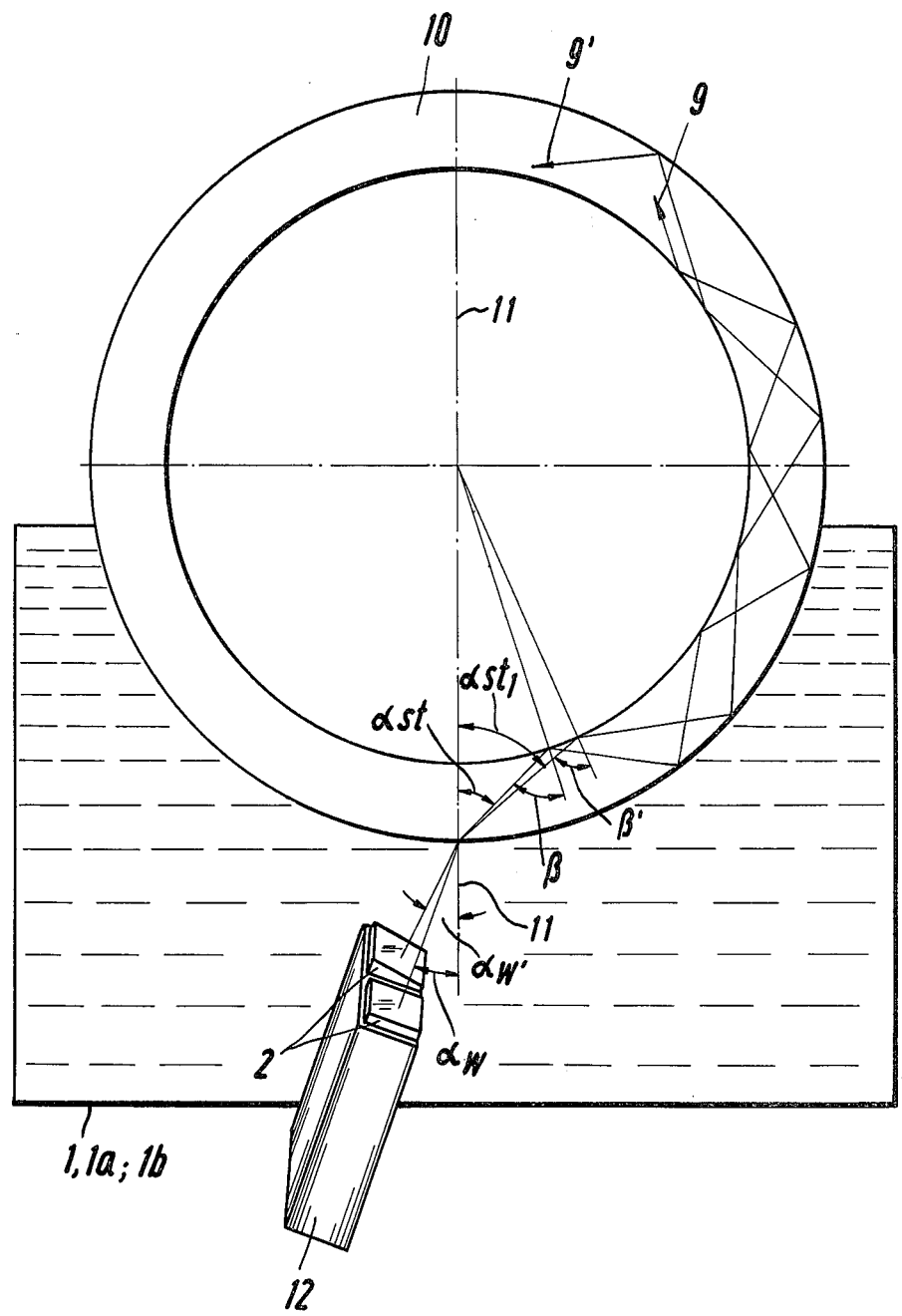
FIG. 3 is a cross-section through a portion of the equipment showing primarily certain angular relations relevant in the system of the preferred embodiment.

Each of these carriages is basically a water tank permitting immersion of a portion of a pipe passing through, provided that particular tank and carriage is placed in the path of the pipe as it is being moved by the roller tracks 4 and 5 through the station. The tanks 1, 1a, and 1b, each include two pairs of transducers, 2 and 2'. The transducers of each pair are mounted in a common holder such as shown in FIG. 3 for the transducers 2 in holder 12. The transducers of the other pair in the same tank, 2', are not shown in FIG. 3, but they are disposed symmetrically to a vertical plane in the tank, being a vertical plane of symmetry for that particular tank. A tank is in test position in the station when its vertical plane of symmetry, as defined, is located so that the axis of a pipe as it is being transported by the roller tracks through the test station, runs in that plane.

Figure 1:
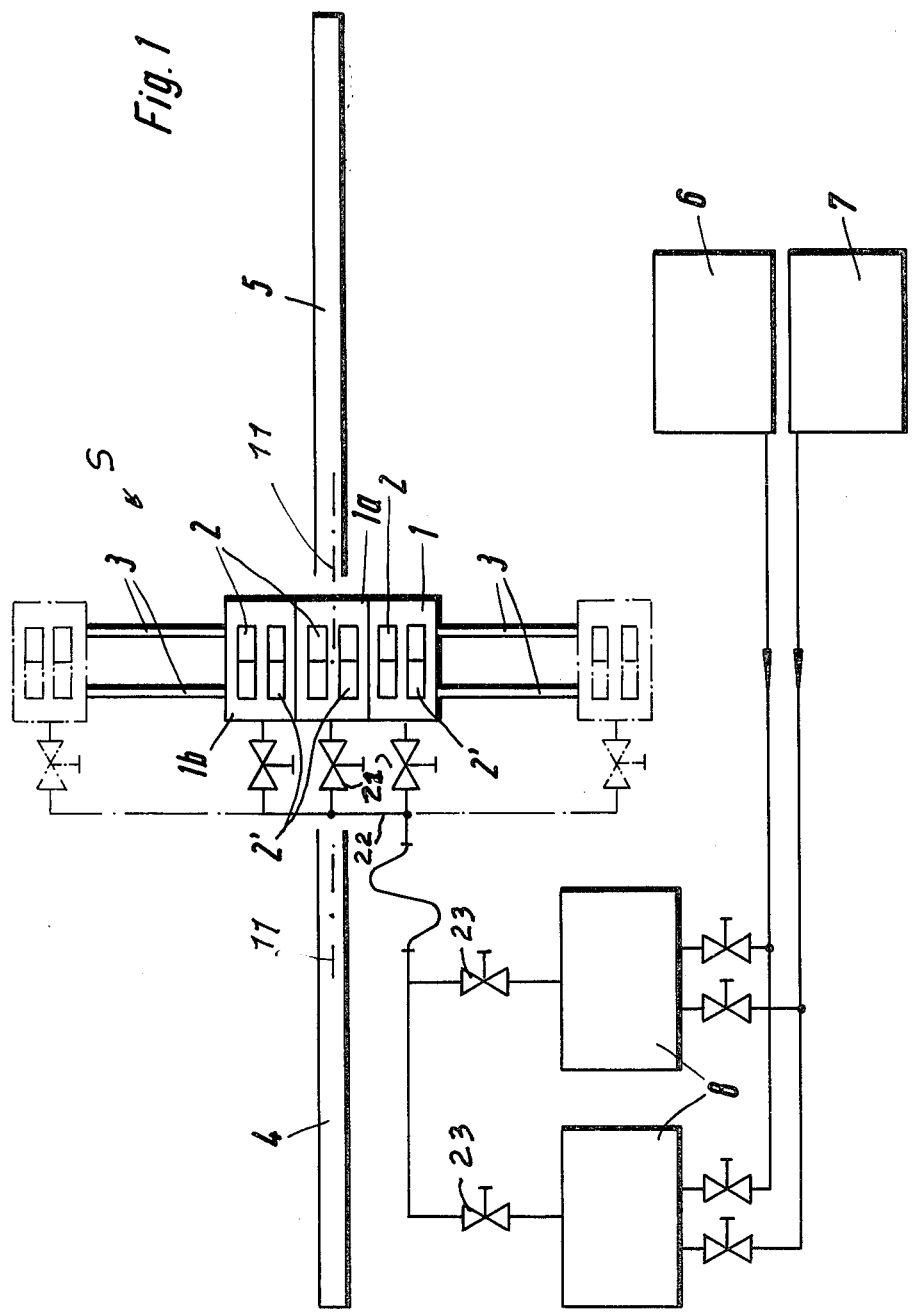
FIG. 1 is a somewhat schematic top view of equipment in which the preferred embodiment of the present invention is practiced.

A particular plane is denoted with reference numeral 11 in FIG. 3 as well as in FIG. 1. However, plane 11 is, in effect, inherent in the roller track and transport equipment, and not in each of these individual test tanks such as 1a, 1b, etc. Thus, it is necessary (a) to position one of these tanks, 1, 1a, or 1b, so that its vertical plane of symmetry, as defined between and by the respective two pairs of transducers 2 and 2', will coincide with the plane 11; it is further necessary (b) to move a pipe through the station so that its axis moves in that plane 11.

Each of these individual transducers, regardless in which tank they are positioned, and regardless whether they pertain to the set 2 or 2', are oriented and fixedly mounted within each of the respective tanks 1, 1a, or 1b, so that the respective transducer radiates a beam towards the pipe whatever its diameter and whatever its wall thickness as it is passing through the station. More specifically, each transducer, 2 or 2', directs an ultrasonic beam at a particular angle $\alpha_w$ to the vertical plane of symmetry of the tank, and if that plane coincides with the vertical plane 11, in which moves the axis of a pipe passing through, then the transducer radiates at that angle $\alpha_w$ in relation to that plane 11. It must now be observed that plane 11 intersects also the pipe's outer surface at the lowest point and the transducers must be positioned so that the particular beam intersects the outer pipe's surface at the point of intersection with plane 11. Therefore, plane 11 defines also the plane of incidence of the radiation test beam, and $\alpha_w$ is, therefore, the angle of incidence of the test beam upon the tube or pipe.

Each of the altogether six transducers 2 establishes a different angle of incident $\alpha_w$ or $\alpha_w'$ as shown in FIG. 3 for two transducers of a pair as mounted in one tank. Of course, for each such transducer 2 there is another one 2', having the same angle of incident but in the opposite orientation as far as the plane 11 is concerned.

By way of example, the six transducers 2 are mounted to their respective tank plane of symmetry to establish respectively the following six angles of incidence:

$\alpha_w$: 23.43°; 22.3°; 20.56°; 19.16°; 17.88°, and 16.99°. These are, of course, the angles of incidence for the respective transducer beams when a pipe has a position in the station so that the vertical plane through the pipe's axis coincides with the tank's plane of symmetry and with the plane 11 as defined by the roller tracks and the station as such.

The test station includes valves 21, one for each of the tanks 1, 1a, 1b, leading to a manifold 22 which, in turn, connects to through valves 23 to either of two mixing tanks 8. Each mixing tank 8 can be charged with hot water from a source 6 or with cold water from a source 7. Suitable metering of the flow of hot and cold water into a mixing tank 8 permits rather rapid establishing of water at a particular temperature. The tanks 8 as well as tanks 1, 1a, 1b, may be equipped with heaters and adjustable thermostat control to maintain the water temperature as having resulted from the initial mixing.

The speed of sound waves and ultrasonic waves through water is greatly dependent upon the temperature. If the angle of incidence of a beam traversing water is constant, the angle of refraction of that beam into the pipe's material depends on the water temperature. Thus, one obtains different angles of refraction, if the water temperature varies. The angle of refraction of the two beams as shown in FIG. 3 are denoted $\alpha_{st}$ and $\alpha_{st}'$. These angles depend on the water temperature for a particular angle of incidence $\alpha_w$ ($\alpha_w'$) in each instance.

The following important aspect should be considered, having been mentioned briefly earlier. First of all, for each specific T/D ratio, one needs a specific orientation for the test beam in the pipe's material, i.e. one needs a specific test angle of refraction $\alpha_{st}$. Secondly, for a fixed orientation of a particular transducer, one can vary the angle of refraction simply by changing the temperature of the water.

Figure 2:
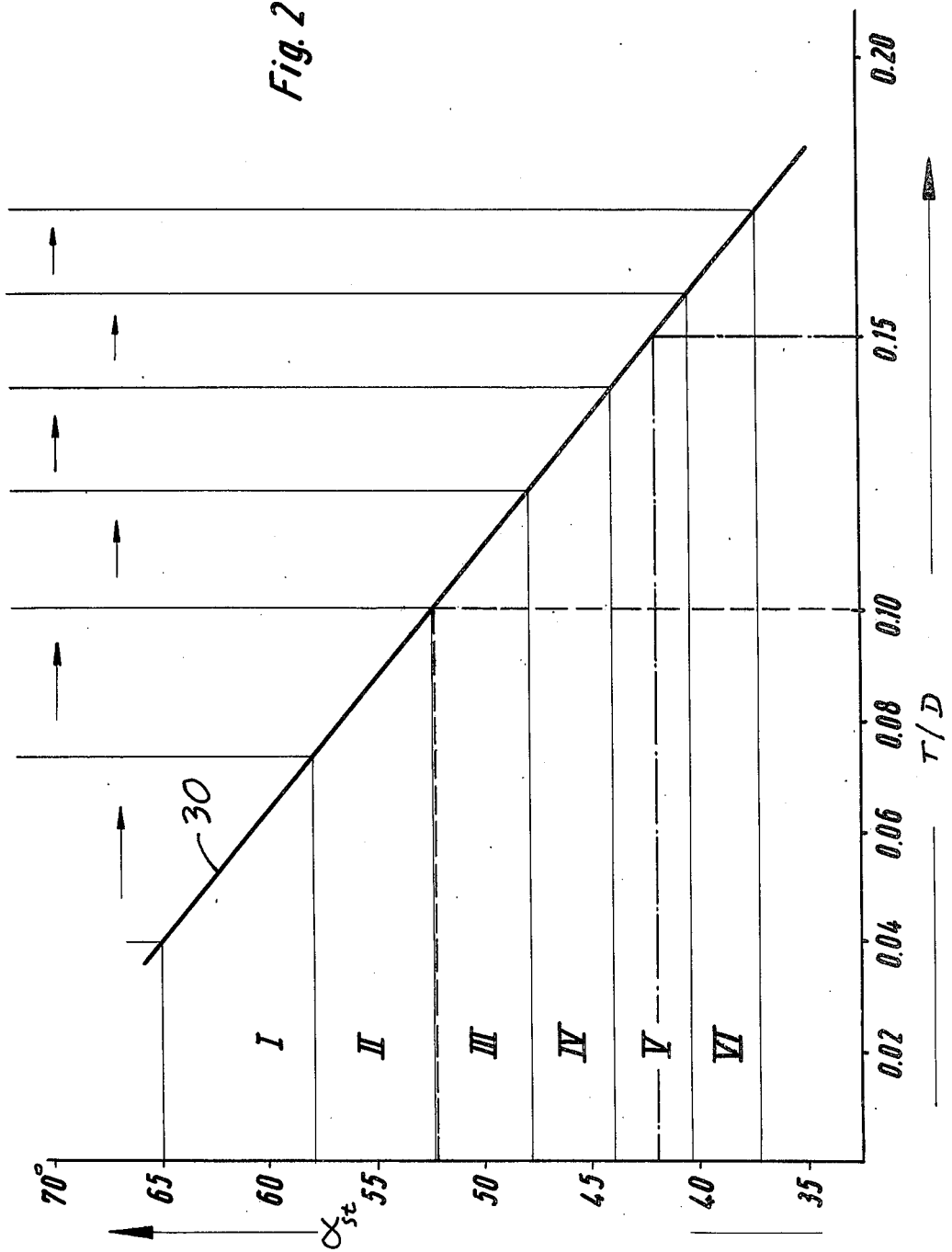
FIG. 2 is a diagram in which test angles of refraction are plotted against wall thickness-to-tube diameter ratios and defining, in addition, several test ranges.

FIG. 2 now shows a number of test ranges which are defined in that each of them is established on the basis of a specific physical orientation to the plane 11. That is to say, the ranges I through VI are associated with transducer adjustments as per the above-identified list for the six angles, from 23.43° to 16.69°. The angles as plotted along the ordinate in FIG. 2 are angles of refraction in steel, $\alpha_{st}$; each range I to VI being specifically defined by a range of such test angles of refraction $\alpha_{st}$. Each range is established through water temperature variations, whereby in each instance the upper limit is associated with 5° tank temperature and the lower limit is associated with 40° C. tank temperature.

The abscissa shows thickness-to-diameter ratios, and the line 30 is the characteristic curve associating these T/D ratios with specific test angles of refraction $\alpha_{st}$ needed for ultrasonic inspection. Consider now the case of T/D ratio of 0.1. The diagram shows that in this particular instance one needs a test angle of refraction $\alpha_{st}$ of 52.4°. In accordance with the diagram, this is the border between test range II and test range III. Test range II is established by a transducer having orientation to produce the angle of incidence $\alpha_w=22.3°$. The lower limit for the test range II as far as angle of refraction is concerned, is at $\alpha_{st}=52.4°$, and requires a water temperature of 40° C. Range III is established by a transducer orientation for an angle of incidence $\alpha_w=20.56°$, and the upper limit for that range requires a tank temperature of about 5° to produce a test angle of refraction of $\alpha_{st}=52.4°$.

It can thus be seen, this particular test angle $\alpha_{st}=52.4$ for an T/D ratio of 0.1 is attainable with two of the transducers 2, one being operated at a high tank water temperature, and the other one at the low tank temperature limit. The situation is somewhat different for a T/D ratio of 0.15. Here, the needed test angle of refraction for the test beam is 42°. This clearly falls into the test range V. The particular transducer is adjusted for an angle of incidence $\alpha_w=17.88°$, and the particular test angle of refraction of $\alpha_{st}=42°$ is obtained by maintaining a bath temperature of 19.7° C.

The individual transducers with vibrators are mounted in pairs in particular holders such as 12, which, in turn, are mounted in a particular orientation in the respective tanks. They are mounted in a fashion for maintaining securely a preadjusted disposition of the resulting direction of a beam as emanating from the transducer. The two transducers have, of course, different orientations within the holder. Preferably, they establish two juxtaposed ranges. For example, tank 1 holds the two transducers for ranges I and II. Tank 1a holds the transducers for ranges III and IV, and tank 1b holes the transducers for ranges V and VI. This means that the two transducers 2 in tank 1 establish angle of incidences $\alpha_w$ of 23.43° and 22.3°. The two transducers 2' in the same tank provide for the same angles $\alpha_w$, but from opposite sides of the vertical plane of symmetry as defined (being plane 11 when the tank is in test position). The other transducers have analogous orientations as can be taken from the list for $\alpha_w$ above.

Generally speaking, the particular examle shown in FIG. 3, depicts two transducers providing, respectively, angle of incidences $\alpha_w$ and $\alpha_w'$ in relation to the normal plane 11 on the bottom portion of the surface of an immersed pipe. Each of them will produce a particular test angle of refraction $\alpha_{st}$, $\alpha_{st}'$, resulting in two different transversal waves, 9 and 9'. Each of these angles $\alpha_{st}$ and $\alpha_{st}'$ can be varied by varying the temperature of the tank water whereby such temperature variation covers a particular range and that gives rise to the test ranges as outlined above. The tank holds a second transducer pair 2' which has been omitted.

It can, thus, be seen that test angles of refractions $\alpha_{st}$ from about 37.3° to about 65° can be obtained by temperature control and under utilization of six transducers with six fixed different angles of incidents ($\alpha_w$), differing from each other by less than two degrees. The six ranges I to VI are, thus, established as follows:

| Ranges | $\alpha_w$ | $\alpha_{st}$(5° C.) | ⟵⟶ | $\alpha_{st}$(40° C.) |
|---|---|---|---|---|
| I | 23.43° | 65° | | 58° |
| II | 22.3° | 58° | | 52.4° |
| III | 20.56° | 52.4° | | 47.9° |
| IV | 19.16° | 47.9° | | 44° |
| V | 17.88° | 44° | | 40.4° |
| VI | 16.69° | 40.4° | | 37.3° |

The system as described operates as follows. First of all, it must be determined what the particular T/D ratio is of a pipe that is about to enter the test stands via the roller track 4. It may be assumed that, for example, the T/D ratio is 0.15. Therefore, the operator knows that he will have to use test range V. He will, therefore, place the particular one of the three tanks, for example tank 1b, into the operating range of the test stand, the others are shifted aside. In addition, he will determine from the chart of FIG. 2 what the particular test angle of refraction $\alpha_{st}$ is; the chart tells him that the needed angle is 42°. He will now choose the desired temperature and obtain the requisite mixture in tank 8 through appropriate metering and timed connection of one of the tanks 8 to the heater 6 and the cooler 7. Having produced the requisite mixture in one of the tanks 8, tank 1b is now charged with the liquid. It may be desirable through control to maintain the temperature of the tank at the desired setting. As the pipe arrives, the operator will conduct the test using the transducer which provides an angle $\alpha_w$ of 17.88°. As stated, the temperature is set to 19.7° and that will produce an angle of refraction of $\alpha_{st}=42°$. The temperature must be maintained constant within the permitted tolerance range which is not too large throughout the test, i.e. throughout the passage of the tube or pipe through the test stand.

If now a pipe of a different T/D ratio is about to arrive, the operator has to determine whether or not the T/D ratio falls within the same test range in which case he does not have to change the test tank. Otherwise, he has to place a different tank into the test stand and proceed as described above.

One can see a modification of the inventive system depending upon the available space. Conceivably, the different test tanks 1, 1a and 1b, may all be permanently positioned in line with the propagation and transport path of the pipes so that a transverse displacement and carriage adjustment is not necessary; one simply operates the respective transducer in that particular tank which in conjunction with a particular tank temperature covers the particular T/D value.

The invention is not limited to the embodiments described above but all changes and modifications thereof not constituting departures from the spirit and scope of the invention are intended to be included.

We claim:

1. In a system for ultrasonic inspection of tubes or pipes using transducer means for providing ultrasonic radiation through a fluid coupler medium towards the surface of a pipe or tube to be refracted at the surface upon entering material of the tube or pipe under a particular test angle of refraction, comprising:

the transducer means being a plurality of transducers having different orientations to an axial plane normal through the surface of a pipe so that radiation launched by the transducers of the plurality have different angles of incidence upon the surface;

tank means in which said transducers are disposed and holding said coupler medium for establishing a refracting interface for ultrasonic radiation with the pipe as directed by the transducers at said orientations; and means for providing coupler fluid to said tank means at adjustable temperatures, so that for each of said transducers and for a similar range of adjustable temperatures, different ranges for the set of refraction result in the pipe, only one transducer of the plurality being used for a particular pipe of particular dimensions to obtain a particular test angle of refraction in one of said ranges of angles.

2. In a system as in claim 1, wherein said means for providing coupler fluid includes a first source for hot water, a second source for cold water, a mixing tank for connection to said first and second sources, and means for connecting the mixing tank to the tank means.

3. In a system as in claim 2, wherein the transducers of the plurality in the different orientations establish angle of incidences which differ by less than 2°.

4. In a system as in claim 1, said tank means including a plurality of individual tanks, each holding at least one transducer;

the system including means for positioning at least one tank of the plurality in a particular position to the pipe being tested.

5. In a system as in claim 1, wherein said means for providing coupler fluid includes means for establishing a coupler fluid temperature from about 5° C. to about 40° C.

* * * * *